United States Patent [19]

Misner

[11] Patent Number: 4,782,152

[45] Date of Patent: * Nov. 1, 1988

[54] DECYANATION OF PERGOLIDE INTERMEDIATE

[75] Inventor: Jerry W. Misner, Indianapolis, Ind.

[73] Assignee: Eli Lilly and Company, Indianapolis, Ind.

[*] Notice: The portion of the term of this patent subsequent to Sep. 20, 2005 has been disclaimed.

[21] Appl. No.: 766,362

[22] Filed: Aug. 16, 1985

[51] Int. Cl.$^4$ ............................................ C07D 457/02
[52] U.S. Cl. ...................................................... 546/67
[58] Field of Search .......................... 546/67; 514/288

[56] References Cited

U.S. PATENT DOCUMENTS 4,246,265 1/1981 Kornfeld et al. .................... 424/261
4,284,775 8/1981 Temme ................................ 544/351

FOREIGN PATENT DOCUMENTS 3667 8/1979 European Pat. Off. ............ 514/288

OTHER PUBLICATIONS

*Organic Synthesis* Coll. vol. I, 2nd. Ed. Wiley, New York (1946).
Elderfield et al., *J. Org. Chem.* 14, 605–637 (1949).
Nickon et al., *J. Am. Chem. Soc.* 74, 5566–5570 (1952).
Robinson, *Can. J. Chem.* 32, 901–905 (1954).
Astill et al., *J. Am. Chem. Soc.* 77, 4079–4084 (1955).
Rapoport et al., *J. Am. Chem. Soc.* 89, 1942–1947 (1967).
Donetti et al., *Tetrahedron Letters* No. 39, 3327–3328 (1969).

*Primary Examiner*—Donald G. Daus
*Assistant Examiner*—Cecilia Shen
*Attorney, Agent, or Firm*—Edward P. Gray; Leroy Whitaker

[57] ABSTRACT

The present invention provides a process for decyanating a pergolide intermediate with an alkali metal hydroxide in an alcoholic solvent having a boiling point greater than about 100° C. at a temperature in the range of about 100° C. to about 175° C.

5 Claims, No Drawings

DECYANATION OF PERGOLIDE INTERMEDIATE

BACKGROUND OF THE INVENTION

The decyanation of substituted cyanamide derivatives represents an important process in synthetic organic chemistry. Typically, this process has been conducted by hydrolyzing the cyanamide in an aqueous acidic medium, but this method is not acceptable for acid labile substrates. Decyanation of cyanamides under alkaline conditions is known in certain instances, but is less preferred, in part because of handling problems which result in an eventual loss in yield of the desired product. See, e.g. *Organic Synthesis* Coll. Vol. I, 201–202 which provides a discussion of the decyanation of diallylcyanamide under acidic and basic conditions.

The present invention relates to a process for decyanating ergoline derivatives with an alkali metal hydroxide in an alcoholic solvent at an elevated temperature. Ergolines have been decyanated by treatment with zinc and acetic acid. See, e.g. U.S. Pat. No. 4,246,265. However, this procedure results in a significant yield reduction because of the formation of impurities, now believed caused by the acid lability of the ergoline substrate. The present process avoids this problem by synthesizing the desired compound in high yield and in pure form in a basic reaction mixture containing an alcoholic solvent.

SUMMARY OF THE INVENTION

The present invention relates to a process for preparing a compound of the formula

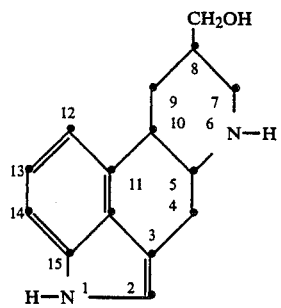

comprising hydrolyzing a cyanamide of the formula

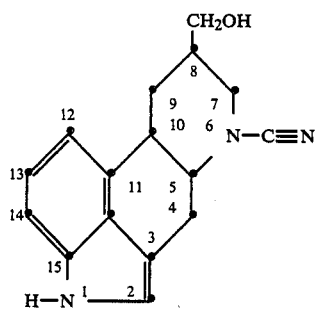

with an alkali metal hydroxide in an alcoholic solvent having a boiling point greater than about 100° C. at a temperature in the range of about 100° C. to about 175° C.

DETAILED DESCRIPTION OF THE INVENTION

Quantities shall be set forth herein in weight units, except for liquids, which are set forth in volume units. All temperatures provided herein are based on standard or atmospheric pressures, or approximately 760 mm pressure. It is well known that raising or lowering the pressure in which a reaction is conducted will result in a higher or lower resulting temperature. As such, it is contemplated that the present process can be carried out under various pressure conditions and that the temperatures recited herein will need to be adjusted accordingly.

This invention provides a process for decyanating 8-(hydroxymethyl)-D-ergoline-6-carbonitrile whereby the compound is hydrolyzed with an alkali metal hydroxide in an alcoholic solvent having a boiling point greater than about 100° C. at a temperature in the range of about 100° C. to about 175° C.

The present process is conducted in the presence of an alkali metal hydroxide, such as potassium hydroxide, lithium hydroxide and especially sodium hydroxide. This hydroxide compound is preferably in a solid or pelletized form. The alkali metal hydroxide will typically be present in the reaction mixture from about an equimolar quantity relative to the starting substrate to about a 5.0 molar excess. The preferred amount of alkali metal hydroxide will be from about 1.5 to about 2.0 molar equivalents for each molar equivalent of starting substrate, and especially 2.0 molar equivalents.

The present process is conducted in an alcoholic solvent having a boiling point greater than about 100° C. at about 760 mm pressure. Exemplary alcoholic solvents include cycloaliphatic alcohols such as cyclohexanol, and preferably polyhydric alcoholic solvents. The term "polyhydric alcoholic solvent", as used herein, represents a solvent having a chemical structure with two or more hydroxy substituents. Typical polyhydric alcohols include cis-2-butene-1,4-diol, trans-2-butene-1,4-diol, ethylene glycol, 1,2-propanediol, 1,3-propanediol, 1,3-butanediol, 2,3-butanediol, 1,4-butanediol and glycerol. Of these, ethylene glycol is the preferred solvent for use in the present process. The concentration of the starting material in the alcoholic solvent is not critical, but it is preferred to employ sufficient solvent to keep the starting material in solution. Larger volumes of solvent are not necessary, but may be employed if desired.

The present process is preferably conducted under standard atmospheric conditions, although the process may also be carried out under an inert atmosphere such as nitrogen or argon in order to limit the amount of water coming in contact with the reaction mixture. Since the product of the present process is insoluble in water, it is desired to minimize the amount of water coming in contact with the reaction mixture.

The process of the present invention is substantially complete after about one to about 24 hours when conducted at a temperature in the range of about 100° C. to about 175° C., more preferably from about 120° C. to about 150° C.

Once the process of the present invention is complete, the product may be isolated according to standard procedures. Typically, the product is isolated by simply adding sufficient water to the reaction mixture to completely precipitate the product from solution. The precipitated solid is then collected, typically by vacuum filtration, and dried as required by standard procedures. The resulting product may be further purified, if desired, by routine procedures such as crystallization from common solvents or chromatography over solid supports such as silica gel or alumina.

The compound prepared by the present process is preferably used as an intermediate in the synthesis of 8β-[(methylthio)methyl]-6-n-propylergoline monomethanesulfonate, generically known as pergolide mesylate. Pergolide mesylate is useful as a prolactin inhibitor and is employed in the treatment of Parkinsonism. See, e.g., U.S. Pat. No. 4,166,182, incorporated by reference, for a discussion of the use and synthesis of pergolide mesylate and related compounds.

The ergoline-8-methanol prepared by the present process may be converted to pergolide mesylate by any number of processes. For example, ergoline-8-methanol is preferably reacted with propionaldehyde in formic acid and DMF to provide the n-propyl ergoline derivative. The hydroxymethyl at C-8 is esterified with a readily replacable group such as a p-toluenesulfonyloxy group or methanesulfonyloxy group in the form of an acid halide or anhydride. This compound is then converted to pergolide by reaction with sodium methylmercaptide, and the resulting compound is converted to the mesylate salt with methanesulfonic acid, or a derivative thereof such as the acid chloride analog.

The compound employed as a starting material in the present process is known and readily prepared by reducing elymoclavine with Raney Nickel in a hydrogen atmosphere, and then demethylating the resulting compound with cyanogen bromide.

The following Examples illustrate specific aspects of the process of the present invention. The Examples are not intended to be limiting to the scope of the invention in any respect and should not be so construed. The identity of the compound prepared by the present process in the following Examples, (8β)-D-ergoline-8-methanol, was determined by thin layer chromatography employing methanol:ethyl acetate:acetic acid (70:30:2, v:v:v) as the eluent as compared to an authentic reference standard.

EXAMPLE 1

A 250 ml three-neck round bottom flask equipped with a thermometer and reflux condenser was charged with 5.34 g (0.02 mol) of (8β)-8-(hydroxymethyl)-D-ergoline-6-carbonitrile, 1.22 g (0.03 mol) of 98.7% pure sodium hydroxide pellets and 50 ml of ethylene glycol. The resulting mixture was heated to approximately 125° C. and an additional 25 ml of ethylene glycol was added. The mixture was heated at approximately 125° C. for 2 hours and slowly cooled to approximately 35° C. To the mixture was added 150 ml of water and the precipitated solid was collected by vacuum filtration. The resulting solid was washed with 75 ml of water and dried in a vacuum oven overnight at 50° C. to provide 4.87 g of (8β)-D-ergoline-8-methanol. Yield 100%. mp=199°–200° C. m/e=242. The purity of the final product was 93.3% as determined by high performance liquid chromatography (HPLC).

EXAMPLE 2

To a 50 ml three-neck round bottom flask equipped with a thermometer and reflux condenser was added 0.53 g (2.0 mmol) of (8β)-8-(hydroxymethyl)-D-ergoline-6-carbonitrile, 0.16 g (4.0 mmol) of sodium hydroxide pellets and 15 ml of ethylene glycol. The resulting mixture was heated at approximately 65° C. for 3 hours and was allowed to stand at about 25° C. for about sixty hours. The mixture was heated at approximately 65° C. for 5 hours and then at about 125° C. for 1½ hours. The mixture was cooled to below 50° C. and 25 ml of water was added. The precipitated solid was collected by vacuum filtration, rinsed with 25 ml of water and dried in a vacuum oven overnight at 50° C. to provide 0.45 g of (8β)-D-ergoline-8-methanol. mp=207°–208° C. Yield 93.6%.

EXAMPLE 3

A 50 ml three-neck round bottom flask equipped with a thermometer and reflux condenser was charged with 1.07 g (4.0 mmol) of (8β)-8-(hydroxymethyl)-D-ergoline-6-carbonitrile, 0.32 g (8.0 mmol) of 98.7% sodium hydroxide pellets and 15 ml of ethylene glycol. The resulting slurry was heated at about 125° C. for about 2 hours and an additional 0.08 g (2.0 mmol) of sodium hydroxide was added. The reaction mixture was cooled to about 45° C. and 30 ml of water was added thereto. The precipitated solid was collected by vacuum filtration and washed with 50 ml of water to provide 0.96 g of (8β)-D-ergoline-8-methanol following drying in a vacuum oven overnight. mp=198°–202° C. Yield 98.9%. The purity of the product was found to be 98.288% by HPLC.

EXAMPLE 4

To a 50 ml three-neck round bottom flask equipped with a nitrogen gas inlet tube thermometer and reflux condenser was added 0.53 g (2.0 mmol) of (8β)-8-(hydroxymethyl)-D-ergoline-6-carbonitrile, 0.4 g (6.0 mmol) of 80% potassium hydroxide pellets and 20 ml of ethylene glycol. The resulting slurry was heated to approximately 125° C. under a nitrogen atmosphere for approximately 16 hours. The reaction mixture was cooled to approximately 75° C. and 30 ml of water was added. The precipitated solid was collected by vacuum filtration, rinsed with 15 ml of water and dried in a vacuum oven at 50° C. to provide 0.47 g of (8β)-D-ergoline-8-methanol. mp=206°–208° C. Yield 97.8%. m/e=242. The purity of the compound was determined by HPLC to be 99.57.

The following Example illustrates the ability of the present process to synthesize the desired compound from impure starting material.

EXAMPLE 5

A 3 l. three-neck round bottom flask fitted with a mechanical stirrer, thermometer and reflux condenser was charged with 133.6 g (0.5 mol) of 82.5% pure (8β)-8-(hydroxymethyl)-D-ergoline-6-carbonitrile, 1.07 l of ethylene glycol and 40.0 g (1.0 mol) of sodium hydroxide pellets. The resulting brown slurry was heated to approximately 130° C. and after 1 hour and 10 minutes the temperature of the reaction mixture was 175° C. The reaction mixture was cooled to approximately 40° C. and 500 ml of water was added. The reaction mixture was cooled to approximately 5° C. with an ice/ethanol external cooling bath and the precipitated solid was collected by vacuum filtration. The isolated solid was washed with 500 ml of water and 200 ml of acetone. The solid was dried overnight at 50° C. in a vacuum oven to provide 110.8 g of 82.7% pure (8β)-D-ergoline-8-methanol. mp=192°–195° C. Yield 91.4%.

The following additional Examples further illustrate the process of the present invention.

EXAMPLE 6

A mixture of 0.53 g (2.0 mmol) of (8β)-8-(hydroxymethyl)-D-ergoline-6-carbonitrile, 0.16 g (4.0 mmol) of sodium hydroxide pellets and 15 ml of propylene glycol was heated at 125° C. for two hours in a three-neck 50 ml round bottom flask. The mixture was cooled to less than 50° C. and 30 ml of water was added. The precipitated solid was collected by vacuum filtration, washed with 30 ml of water and dried under a vacuum oven at 50° C. overnight to provide 0.3 g of (8β)-D-ergoline-8-methanol. mp=186°-188° C. Yield 62.4%. The purity of the solid was determined by HPLC to be 91.42%.

EXAMPLE 7

A 50 ml three-neck round bottom flask was charged with 0.53 g (2.0 mmol) of (8β)-8-(hydroxymethyl)-D-ergoline-6-carbonitrile, 0.16 g (4.0 mmol) of sodium hydroxide pellets and 15 ml of glycerol. The resulting mixture was heated to approximately 125° C. for 2 hours and cooled. The reaction mixture was combined with 30 ml of water and the precipitated solid was collected by vacuum filtration, washed with 30 ml of water and dried in a vacuum oven at 50° C. overnight. The solid was 87.864% pure (8β)-D-ergoline-8-methanol and weighed 0.48 g. Yield 99.9%. mp=180°-183° C.

EXAMPLE 8

A mixture of 0.53 g (2.0 mmol) of (8β)-8-(hydroxymethyl)-D-ergoline-6-carbonitrile, 0.16 g (4.0 mmol) of sodium hydroxide pellets and 15 ml of cyclohexanol was heated at 125° C. for two hours in a three-neck 50 ml round bottom flask. The mixture was cooled to less than 50° C. and 30 ml of water was added. The precipitated solid was collected by vacuum filtration, washed with 30 ml of water and dried under a vacuum oven at 50° C. overnight to provide 0.32 g of (8β)-D-ergoline-8-methanol. mp=204°-206° C. Yield 66.6%. The purity of the solid was determined by HPLC to be 84.7%.

The following Examples illustrate the large scale application of the process of the present invention.

EXAMPLE 9

A 22 l. four-neck round bottom flask fitted with a thermometer and reflux condenser was charged with 913.5 g (3.42 mol) of (8β)-8-(hydroxymethyl)-D-ergoline-6-carbonitrile, 276.0 g (6.9 mol) of sodium hydroxide pellets and 10 l. of ethylene glycol. The reaction mixture was heated at approximately 130° C. for 2 hours and cooled to a temperature less than 100° C. To the reaction mixture was added 5.0 l. of water and the reaction mixture was cooled to about 25° C. The precipitated solid was collected by vacuum filtration and washed with 8 l. of water, followed by 1 l. of diethyl ether. The solid was dried overnight in a vacuum oven at 70° C. to provide 809.0 g of (8β)-D-ergoline-8-methanol. Yield 97.7%.

Three additional reactions were set up as generally described above in Example 9 to provide an additional 2,446 g of the desired compound. The total yield of the four reactions was 3,255 g of (8β)-D-ergoline-8-methanol. Yield 98.3%.

The following process illustrates the synthesis of pergolide mesylate from the product of the present process prepared in Example 9.

A. (8β,D)-6-Propylergoline-8-methanol

A 22 l. three-neck round bottom flask was charged with 1085 g (4.48 mol) of (8β)-D-ergoline-8-methanol and 6.71 l. of N,N-dimethylformamide. To the solution was slowly added 967 ml of propionaldehyde while maintaining the temperature of the reaction mixture between about 25° C. and about 30° C. with an external cold water bath. Next, 1020 ml of formic acid was added and the reaction mixture was allowed to stir at room temperature for two hours. The mixture was held overnight, and then stirred at about 80° C. for one hour and 15 minutes. The mixture was cooled and poured into a solution containing 21 l. of water, 1.9 l. of 50% sodium hydroxide and 14 l. of ethyl acetate. The pH of the mixture was adjusted to about 8.0 with an additional 800 ml of 50% sodium hydroxide. The organic layer was separated and the aqueous phase was extracted with 2 l. of ethyl acetate. The organic layers were combined and washed with two 2 l. portions of an aqueous sodium chloride solution. The organic phase was combined with 650 g of decolorizing carbon and stirred for 30 minutes. The mixture was gravity filtered and held for further processing.

Two additional runs were conducted in general as described above. The three organic solutions were combined and concentrated under vacuum. The residue was dissolved in 34 l. of acetone and the solution was divided in half. Each solution was combined with 436 ml of methanesulfonic acid and stirred overnight at about 0° C. to about 5° C. The two solutions were combined and filtered. The solid was washed with 6 l. of acetone and dried. The solid was combined with 8 l. of water and the mixture was combined with 8 l. of ethyl acetate. The mixture was made basic with 850 ml of 50% sodium hydroxide. The organic phase separated and the aqueous layer was extracted with 2 l. of ethyl acetate. The organic layers were combined and concentrated under vacuum to provide 2742 g of (8β,D)-6-propylergoline-8-methanol.

B. (8β)-6-Propyl-D-ergoline-8-methanol, methanesulfonate

To a 22 l. four-neck round bottom flask was added 2742 g (9.64 mol) of (8β,D)-6-propylergoline-8-methanol and 15.4 l. of pyridine under a nitrogen atmosphere. The mixture was cooled to about 10° C. and 1720 g (15.0 mol) of methanesulfonyl chloride was added dropwise over a period of about 90 minutes while maintaining the temperature of the reaction mixture below about 35° C. The mixture was stirred for 90 minutes at about 20° C. to about 25° C. and poured into a solution of 64 l. of water and 1200 ml of ammonium hydroxide. The pH of the mixture was adjusted to about 10.0 with an additional 300 ml of ammonium hydroxide. The mixture was stirred for two hours and filtered. The collected solid was washed with 16 l. of water and dried to provide 3209 g of (8β)-6-propyl-D-ergoline-8-methanol, methanesulfonate.

C. (8β)-8-[(Methylthio)methyl]-6-propyl-D-ergoline

To a 22 l. four-neck round bottom flask was added a solution of 232 ml of methanethiol in 2 l. of N,N-dimethylformamide in one portion. Next, 224 g of sodium methoxide was added to the reaction mixture held at a temperature in the range of about 0° C. to about −5° C. over a period of about 30 minutes. To this mixture was added a solution of 1070 g (2.95 mol) of (8β)-6-propyl-D-ergoline-8-methanol, methanesulfonate and 10.3 l. of N,N-dimethylformamide over a period of about one hour while maintaining the temperature of the mixture below about 5° C. The mixture was stirred overnight at room temperature and warmed to 90° C. for one hour. The mixture was combined with water and filtered. Two additional reactions were conducted concurrently with the process described above. The combined solids were washed with water and dried to provide 2680 g of (8β)-8-[(methylthio)methyl]-6-propyl-D-ergoline.

D. Pergolide mesylate

Five separate reactions were conducted essentially as follows. A 22 l. four-neck round bottom flask was charged with 536 g (1.7 mol) of (8β)-8-[(methylthio)methyl]-6-propyl-D-ergoline and 15 l. of methanol. The mixture was heated to reflux and 256 ml of methanesulfonic acid was added dropwise over a period of about 30 minutes. To the mixture was added 170 g of Darco and the mixture was refluxed for 30 minutes. The mixture was filtered and the filtrate was combined with the filtrates from the four other reactions. The mixture was concentrated and filtered to provide 1355.5 g of solid. The solid was combined with 16 l. of methanol and the resulting solution was cooled. The mixture was filtered and dried to provide 2360 g of pergolide mesylate.

I claim:

1. A process for preparing a compound of the formula

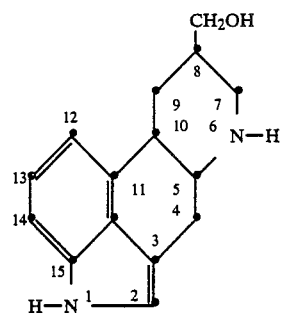

comprising hydrolyzing a cyanamide of the formula

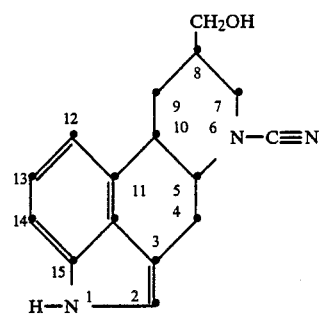

with an alkali metal hydroxide in an alcoholic solvent having a boiling point greater than about 100° C. at a temperature in the range of about 100° C. to about 175° C.

2. A process of claim 1 wherein the alcoholic solvent is a polyhydric alcoholic solvent.

3. A process of claim 2 wherein the polyhydric alcoholic solvent is ethylene glycol.

4. A process of claim 3 wherein the alkali metal hydroxide is potassium hydroxide.

5. A process of claim 3 wherein the alkali metal hydroxide is sodium hydroxide.

* * * * *